United States Patent [19]

Le Van Mao

[11] Patent Number: 4,615,995

[45] Date of Patent: Oct. 7, 1986

[54] ZEOLITE CATALYSTS

[75] Inventor: Raymond Le Van Mao, Montreal, Canada

[73] Assignee: The Asbestos Institute, Montreal, Canada

[21] Appl. No.: 688,639

[22] Filed: Jan. 3, 1984

[51] Int. Cl.$^4$ .......................... B01J 29/28; B01J 21/16
[52] U.S. Cl. .......................................... 502/64; 502/71
[58] Field of Search .............................. 502/64, 71, 77

[56] References Cited

U.S. PATENT DOCUMENTS

| | | | |
|---|---|---|---|
| 3,790,471 | 2/1974 | Argauer et al. ................... | 502/71 X |
| 3,914,171 | 10/1975 | Schoennagel ....................... | 208/135 |
| 4,180,516 | 12/1979 | Chang et al. ........................ | 502/71 |
| 4,349,461 | 9/1982 | Chu et al. ............................ | 502/77 |
| 4,511,667 | 4/1985 | Le Van Mao et al. ............... | 502/64 |

*Primary Examiner*—Carl F. Dees
*Attorney, Agent, or Firm*—Cushman, Darby & Cushman

[57] ABSTRACT

Improved yield in light olefins and aromatics from methanol conversion on Zn and Mn loaded pentasil zeolite and composite pentasil zeolite-asbestos catalysts, the Zn content thereof ranging from 0.1 to 1.0% wt/wt and the Mn content thereof ranging from 0.2 to 5.0% wt/wt. The light olefins/aromatics ratio in the products varies with the Mn content in the catalyst, the cumulative light olefinic and aromatic production being kept constant at a high value (higher than 80% at 450° C.).

6 Claims, No Drawings

ZEOLITE CATALYSTS

PRIOR ART—BACKGROUND OF THE INVENTION

Because of large availability of methanol in the industrial world, it has for many years been considered as the most desirable material for obtaining light olefins, aromatic and non-aromatic liquids in the gasoline boiling range. Methanol is also the intermediate of the process starting from synthesis gas. This synthesis gas (a mixture of carbon monoxide and hydrogen) can be derived from natural gases, biomass, coal or heavy oils.

Since light olefins and liquid hydrocarbons (in particular, aromatics) are the most commercially valuable products in the catalytic conversion of methanol and dimethyl ether (dehydration derivative of methanol), high yields in such hydrocarbons are desired in the industrial viewpoint.

Many attempts have been done to find the ideal catalyst. Crystalline aluminosilicate zeolites are the most indicated for this purpose, due mainly to their ordered and molecular-sized framework structure. Among them, the ZSM-5 type zeolites show high performances both in terms of methanol conversion and product selectivities. However, under normal reaction conditions, light paraffin production occurs for more than the third of the hydrocarbon yield as can be seen from Table 1.

a high production of light paraffins and a very low production of light olefins (see Table 1).

Modifications of the zeolite chemical composition by incorporating extraneous components lead to one of these two product distributions:

(a) large production of light olefins with significant (or smaller) production of light paraffins, negligible (or much reduced) production of aromatic and non-aromatic liquid hydrocarbons. For this category, we can mention the ZSM-5 zeolite promoted with trimethylphosphite or modified with silica, and the 13X zeolite bearing Mg and Mn (see Table 1). One of the drawbacks of these catalysts is their relatively low methanol conversion within the range of reaction temperature (370°–450° C.); or their very reduced yield in liquid hydrocarbons;

(b) large production of liquid hydrocarbons (with a relatively high aromatic content), and significant production of light paraffins and a very reduced production of light olefins.

For this category, we can mention the case of the ZSM-5 zeolite into which is incorporated Zn or an ion of one among the following groups: $I_b$, $II_a$, $II_b$, $III_a$, $IV_a$ or VIII (see Table 1).

OBJECTS OF THE PRESENT INVENTION

An ideal catalytic system for the conversion of methanol into hydrocarbons do have all the following catalytic performance under normal reaction conditions as

TABLE 1

| | The prior art | | | | | | | | |
|---|---|---|---|---|---|---|---|---|---|
| | Reaction Conditions | | Methanol conversion into hydrocarbons (%)[1] | Product selectivities (%) | | | | Ole + Liq (liq = Ar + C5+) | Ole + Ar | Ole/Ar |
| Catalyst | T (°C.) | Press. (atm) | | $C_1$–$C_4$ Paraffins | $C_2$–$C_4$ olefins (Ole) | Aromatics (Ar) | Non-Aromatics ($C_5$+) | | | |
| ZSM-5 zeolite (A) | 427 | 1 | 99 | 42 | 10 | 41 | 7 | 58 | 51 | 0.3 |
| | 427 | 0.25 | 99 | 22 | 38 | 20 | 20 | 78 | 58 | 1.8[2] |
| | 427 | 0.07 | 99 | 15 | 78 | 2 | 5 | 85 | 80 | 39.0[2] |
| ZSM-5 Zeolite (B) | 371 | 1 | 99 | 35[3] | 3[3] | 41 | 21 | 65 | 44 | 0.1 |
| ZSM-5 Zeolite promoted with trimethylphosphite | 385 | 1 | 31 | 5 | 39 | 20 | 36 | 95 | 60 | 1.9 |
| | 465 | 1 | 88 | 4 | 62 | 8 | 26 | 96 | 70 | 7.8 |
| (C) | 560 | 1 | 99 | 5 | 66 | 12 | 16 | 94 | 78 | 5.5 |
| 13X Zeolite bearing Mg and Mn (D) | 400 | 1 | 91 | 19 | 81 | — | — | 81 | 81 | ∞[4] |
| ZSM-5 Zeolite with incorporation of one metal of group $I_b$, $II_a$, $II_b$, $III_a$, $IV_a$ or VIII (E) | 400 | 1 | 99 | (NR) (31) | (NR) | 37 | 32 | NR | NR | NR[5] |

REMARKS:
[1]Carbon atom basis
[2]Subatmospheric pressure of methanol
[3]reported in Chang C.D. et al J. Cat. 86, 289 (1984)
[4]no liquid hydrocarbons produced
[5]not reported but likely similar to the case of U.S. Pat. No. 3,894,103
PATENTS:
(A) U.S. Pat. No. 4,025,575 (Mobil Oil)
(B) U.S. Pat. No. 3,894,103 ($SiO_2/Al_2O_3$ = 100) (Mobil Oil)
(C) U.S. Pat. No. 3,911,041 (Mobil Oil)
(D) Ger. Offen 2,755,229 (Hoeschst A.G.)
(E) U.S. Pat. No. 3,894,104 (example 6, Zn) (Mobil Oil).

Modifications of reaction parameters (for example, by using very low-subatmospheric partial pressure of methanol) can decrease the light paraffin production and increase the light olefin yield. However, not only the aromatic formation is also depressed (see Table 1), but also the methanol conversion per pass per unit weight of catalyst is very limited.

Modifications of the catalyst characteristics (for example $SiO_2/Al_2O_3$ ratio) leads to a high liquid hydrocarbon yield with relatively high aromatic content and tested for the parent ZSM-5 zeolite (i.e. atmospheric pressure, temperature ranging from 370° to 450° C., WHSV ranging from 0.1 to 10 $hr^{-1}$):

(1) high methanol conversion into hydrocarbons, close to 100% (carbon atom based calculation);

(2) low gaseous paraffin production;

(3) high cumulative production of light olefins and liquid hydrocarbons, i.e. equal to or more than 90%;

(4) high cumulative production of light olefins and aromatics;

(5) (a) equilibrated production of light olefins and aromatics, i.e. Ole/Ar ratio close to 1; and The catalytic performances are illustrated in Table 2.

TABLE 2

| Catalyst | Zn (%) | Mn (%) | Reaction conditions T (°C.) | Reaction conditions pressure (atm)[1] | Methanol conversion into hydrocarbons[2] | Product selectivities (%) $C_1$-$C_4$ Paraffins | Product selectivities (%) $C_2$-$C_4$ Olefins (Ole) | Product selectivities (%) Aromatics (Ar) | Product selectivities (%) Non-Aromatics ($C_5^+$) | Ole + Liq. (Liq = Ar + $C_5^+$) | Ole + Ar | Ole/Ar |
|---|---|---|---|---|---|---|---|---|---|---|---|---|
| Zn—Mn doped ZSM-5 zeolite | 0.37 | 1.17 | 400 | 0.9 | 99 | 11 | 37 | 31 | 21 | 89 | 68 | 1.2 |
| | | | 450 | 0.9 | 93 | 6 | 46 | 33 | 15 | 94 | 79 | 1.4 |
| Zn—Mn doped composite ZSM5/asbestos cat. (high MLD)[3] | 0.23 | 1.10 | 400 | 0.9 | 99 | 10 | 37 | 34 | 19 | 90 | 71 | 1.1 |
| | | | 450 | 0.9 | 98 | 7 | 43 | 39 | 11 | 93 | 82 | 1.1 |
| | 0.23 | 2.08 | 400 | 0.9 | 98 | 7 | 47 | 21 | 25 | 93 | 68 | 2.2 |
| | | | 450 | 0.9 | 97 | 5 | 50 | 32 | 13 | 95 | 82 | 1.6 |
| Zn—Mn doped composite ZSM5/asbestos cat. (Med. MLD)[3] | 0.32 | 1.60 | 400 | 0.9 | 91 | 5 | 50 | 18 | 27 | 95 | 68 | 2.8 |
| | | | 450 | 0.9 | 86 | 6 | 51 | 25 | 18 | 94 | 76 | 2.0 |

[1]total pressure = 1 atm (balance with nitrogen)
[2]carbon atom basis (%)
[3]magnesium leaching degree. High MLD >90%. Medium MLD = 80 + 90%.

(b) possibility of shifting this Ole/Ar ratio to higher value, without changing the previous figure, i.e. keeping (1), (2), (3) and (4) constant.

SUMMARY OF THE INVENTION

The present invention relates to novel metal loaded zeolite catalysts selected from pentasil zeolite ZSM-5 and pentasil zeolite-asbestos composite catalyst.

The pentasil zeolite ZSM-5 catalyst is characterized by having a portion of its internal acid reaction sites replaced with zinc ions and by having manganese ions absorbed on the external surface of the zeolite.

On the other hand, the pentasil zeoliteasbestos composite catalyst comprises a pentasil zeolite within a magnesium and iron leached asbestos micromatrix and is characterized by having a small portion of the internal acid reaction sites of the pentasil zeolite replaced by zinc ions and by having manganese ions absorbed on the external surface thereof while the magnesium and iron leached asbestos micro-matrix is doped internally with zinc ions and externally with manganese ions. In each of the novel catalysts of the present invention the amount of zinc varies from 0.1 to 1.0% w/w of the metal content while the amount of manganese varies from 0.2 to 5% w/w of the metal content.

A definition of pentasil is to be found in an article entitled "Pentasil family of high silica crystalline materials" in Proc. Conf. London (April 1979, p. 133-139).

The novel concept of loading Zn and Mn onto ZSM-5 zeolite or onto composite ZSM-5 zeolite/asbestos materials leads to the following catalytic performances at 400° C. and 450° C. under atmospheric pressure and at 2.4 hr$^{-1}$ as WHSV (see Table 2):

(1) methanol conversion into hydrocarbons close to 100% or at least higher than 85% (carbon atom based calculation);

(2) light paraffin selectivity lower than 10%;

(3) cumulative selectivity of light olefins and liquid hydrocarbons, equal to or higher than 90%;

(4) cumulative selectivity of light olefins and aromatics:
  (a) close to 70% at 400° C.;
  (b) equal to or higher than 80% at 450° C.;
  (a) Ole/Ar=1.1 with moderate Mn loading;
  (b) Ole/Ar higher than 1.1 with higher Mn loading, without changing items (1), (2), (3) and (4).

The present invention also relates to the conversion of methanol (or dimethyl ether) into hydrocarbons over Zn and Mn loaded catalysts of the zeolite type.

The invention also is concerned with the high cumulative production of light olefins and gasoline boiling range hydrocarbons having a high content in aromatics. It is also a feature of the present invention to provide a catalytic system capable of giving a distribution which can be changed from an equilibrated production of light olefins and aromatics to a light olefin richer production, the cumulative production of light olefins and aromatics being kept constant at a high value. To achieve this product distribution change, it is sufficient to monitor the Mn content in the final catalyst.

The zeolites which are directly concerned by the present invention belong to the family called ZSM or pentasil zeolite family, namely ZSM-5 type zeolites.

The basic zeolite system can be a pure ZSM-5 zeolite under acid form (H-ZSM-5) or a composite ZSM-5 zeolite/asbestos material. The latter composite material is prepared by a multi-step process which includes the partial leaching of the metallic components (magnesium and iron) from the chrysotile asbestos fibres, followed by the "in situ" zeolite crystallization and ended by the incorporation of the acid sites into the zeolite lattice.

The Zn loading into the zeolite catalysts is performed under ion-exchange conditions. While H-ZSM-5 material requires very severe exchange conditions to obtain the desired content in Zn ions, the composite ZSM-5/asbestos material needs very mild conditions for incorporating Zn ions with the desired content. It is expected that with H-ZSM-5 zeolite, the $Zn^{2+}$ ions do replace some of the acid sites mainly located within the zeolite pores.

On the other hand, it is found that with the composite ZSM-5/asbestos material, the loading of Zn ions was accompanied by an important loss of Fe ions (the Mg content remained substantially constant): this means that a small part of Zn ions was exchanged with the acid sites of the zeolite component while a large part of these ions was incorporated into the remnants of the chrysotile asbestos.

The Mn loading was simply performed by dry impregnation of a solution of manganese salt onto the Zn-loaded catalyst.

To achieve the desired catalytic performance, in both cases the Zn metal content of the final catalysts must be less than 1% (wt/wt of catalyst), preferably between 0.1% (wt/wt) and 0.6% (wt/wt) and most preferably between 0.1 and 0.3%. The Mn metal content must be at least 0.2% (wt/wt), up to 5% (wt/wt) and preferably up to 2.5% (wt/wt).

The Ole/Ar ratio depends strongly on the Mn/Zn weight or atom ratio. For example, under reaction conditions as described in the section previously and with catalysts which exhibit a Mat/Al ratio of about 30/1, the following dependance can be exemplified for a Zn content of 0.2 to 0.4% wt/wt: Mn/Zn=2 (weight basis)=2.3 (atom basis), most of the present catalysts exhibit a Ole/Ar ratio close to 1. Mn/Zn=8 (weight basis)=9.5 (atom basis), most of the present catalysts exhibit a Ole/Ar ratio close to 2.

DESCRIPTION OF THE INVENTION

The basic composite pure pentasil ZSM-5 zeolite and pentasil ZSM-5 zeolite-asbestos composite catalysts of the present invention are prepared according to the following procedure:

Composite ZSM-5 Zeolite/asbestos Material

The fibrous asbestos used in the examples of the present invention is of type 7TF-12 chrysotile asbestos, with short fibres, but the present procedure for preparing and testing the pentasil zeolite-asbestos composite catalysts is applicable to all other types of fibrous asbestos.

The starting material, 7TF-12 asbestos, has the following composition (% by weight):
$SiO_2$:42.8%
MgO:50.2%
$Fe_2O_3$:6.6% (under FeO and $Fe_3O_4$ forms)
$Al_2O_3$:0.1%
$Na_2O$:0.1%

The catalyst is prepared by partially leaching the magnesium (and the iron) out of the asbestos materials by acid attack.

In particular, aqueous solutions of HCl are used to perform the leaching operation. Table 3 reports the conditions of preparation and the composition of the leached asbestos (Alix).

depends on the acid treatment conditions. Thus, by controlling the magnesium leaching operation conditions, it is possible to obtain a predetermined magnesium leaching degree.

The following example can be considered as typical procedure for the magnesium leaching step: 100 g of chrysotile asbestos fibres (7TF-12 grade) were suspended in a solution prepared from 200 ml of concentrated HCl and 800 ml of distilled water.

The suspension was heated at 70°–80° C. with rapid stirring for 2.5 hours. Then, 2000 ml of distilled water were added and the resulting suspension was allowed to stand for 12 hours at room temperature. The suspension was filtered and washed with 2 liters of distilled water at room temperature. The solid was dried at 120° C. for 12 hours and the chemical composition of the resulting material, called Alix 017, is reported in Table 3.

The magnesium leaching degree (MLD) of the Alix (Table 3) is defined as:

$$(MLD) = \frac{(MgO)_i - (MgO)_f}{(MgO)_i} \times 100(\%)$$

where $(MgO)_i$ and $(MgO)_f$ are the magnesium contents (dried oxide basis) of the asbestos fibres and of the Alix, respectively.

ZSM-5 zeolite was crystallized using the Alix as starting material. To have the required conditions for preparing efficient catalysts for the conversion of methanol, sodium aluminate was added to the suspension which contains also NaOH and tetrapropylammonium ion (TPA) as synthesizing agent for the ZSM-5 zeolite.

The following example can be considered as typical procedure for the step of the ZSM-5 zeolite crystallization:

25.0 g of the Alix 017 were suspended in a solution prepared from 40.0 g of tetrapropylammonium bromide (TPA Br from Fisher Sc. Co., >98%) and 2.5 g of NaOH (Fisher Sc. Co.) dissolved in 160 ml of distilled water. The suspension was heated at 70°–80° C. for 1 hour under vigorous stirring. Then, a solution of 1.5 g of sodium aluminate (Fisher Co., % weight composi-

TABLE 3

| | | | | | | | Preparation of leached asbestos and (Alix) | | | | |
|---|---|---|---|---|---|---|---|---|---|---|---|
| | Amount of 7TF-12 | | | Heating | | | Product | | | | |
| | asbestos | HCl solution | | Time | (dehyd) | $SiO_2$ | $Al_2O_3$ | $Na_2O$ | MgO | $Fe_2O_3$ | MLD |
| ALIX | (g) | N | ml | (80° C.) | g | (%) | (%) | (%) | (%) | (%) | (%) |
| 001/2 | 100 | 3.0 | 1000 | 7.0 hr | 40 | 98.2 | 0.36 | 0.14 | 1.06 | 0.28 | 98 |
| 013 | 100 | 2.4 | 1000 | 4.5 hr | 44 | 89.0 | 0.51 | 0.14 | 4.14 | 6.22 | 92 |
| 025 | 200 | 3.0 | 2000 | 5.0 hr | 87 | 90.6 | 0.32 | 0.14 | 2.95 | 2.57 | 94 |
| 020/2 | 100 | 2.4 | 1000 | 4.0 hr | 42 | 91.8 | 0.38 | 0.14 | 3.38 | 4.35 | 93 |
| 024 | 120 | 2.4 | 1200 | 3.5 hr | 53 | 88.0 | 0.35 | 0.13 | 5.88 | 5.65 | 88 |
| 018/1 | 100 | 2.4 | 1000 | 3.5 hr | 45 | 85.2 | 0.36 | 0.16 | 6.60 | 7.65 | 87 |
| 018/2 | 100 | 2.4 | 1000 | 3.5 hr | 43 | 86.1 | 0.32 | 0.14 | 6.23 | 7.15 | 88 |
| 027 | 150 | 2.4 | 1500 | 2.5 hr | 71 | 82.6 | 0.43 | 0.19 | 9.39 | 7.68 | 81 |
| 030 | 150 | 2.4 | 1500 | 2.5 hr | 69 | 83.7 | 0.22 | 0.16 | 8.99 | 6.98 | 82 |
| 017 | 100 | 2.4 | 1000 | 2.5 hr | 41 | 81.8 | 0.45 | 0.12 | 10.10 | 7.59 | 80 |
| 016 | 100 | 2.4 | 1000 | 1.25 hr | 47 | 82.0 | 0.18 | 0.13 | 10.53 | 7.20 | 80 |

The leaching of magnesium via strong mineral acid treatment and under drastic conditions (high concentration in acid, several hours heating) can solubilize most of the magnesium (and other metallic components) leaving behind a collapsed macro-structure of geliform silica. Mild acid treatment with diluted aqueous solutions of strong mineral acids or attack with weak acids like acetic acid, oxalic acid, etc., may preserve the chrysotile macro-structure, the magnesium content of which tion: $Al_2O_3$=46.8%; $Na_2O$=28.4) in 20 ml of distilled water was added. Heating was continued at 70°–80° C. with vigorous stirring for 10 minutes.

The suspension was transferred into a polypropylene bottle which was then put into a Sparr autoclave and heated at 170° C. (±5° C.) for 10 days.

After cooling, the suspension was discharged and filtered; the solid was washed with distilled water until the washing liquid had a pH lower than 9 and then dried at 120° C. for 12 hours and finally activated in the air at 550° C. for 12 hours. The resulting material, called A-48, was a precursor for the composite catalyst HA-48.

Table 4 reports the conditions for synthesizing the ZSM-5 zeolite component in the composite catalyst precursors (A).

TABLE 4

| Catalyst Precursor | Alix | W (g) | Silica gel (g) | Na aluminate (g) | TBA Bromide (g) | NaOH (g) | Added Water (ml) | Synthesis T (°C.) | days | Product[3] (g) |
|---|---|---|---|---|---|---|---|---|---|---|
| P-38 | — | — | 44[1] | 1.5 | 40 | 2.5 | 160 | 170 | 10 | 22.4 |
| P-68 | — | — | 25[2] | 1.8 | 40 | 2.5 | 160 | 170 | 10 | 24.4 |
| A-39 | 001/2 | 24.0 | — | 1.5 | 40 | 2.5 | 180 | 170 | 10 | 20.0 |
| A-45 | 013 | 24.1 | — | 1.5 | 40 | 2.5 | 180 | 170 | 10 | 19.4 |
| A-62 | 025 | 35.0 | — | 2.0 | 40 | 2.5 | 180 | 170 | 10 | 30.3 |
| A-56 | 020/2 | 25.0 | — | 1.5 | 40 | 2.5 | 180 | 170 | 10 | 21.3 |
| A-58 | 024 | 45.0 | — | 2.7 | 40 | 2.5 | 180 | 170 | 10 | 46.5 |
| A-49 | 018/1 | 25.0 | — | 1.5 | 40 | 2.5 | 180 | 170 | 10 | 21.1 |
| A-54 | 018/2 | 30.0 | — | 1.8 | 40 | 2.5 | 180 | 170 | 10 | 25.3 |
| A-64 | 027 | 35.0 | — | 2.0 | 40 | 2.5 | 180 | 170 | 10 | 30.7 |
| A-69 | 030 | 66.0 | — | 4.2 | 80 | 5.0 | 360 | 170 | 10 | 56.7 |
| A-48 | 017 | 25.0 | — | 1.5 | 40 | 2.5 | 180 | 170 | 10 | 20.4 |
| A-60 | 016 | 35.0 | — | 2.0 | 40 | 2.5 | 180 | 170 | 10 | 31.8 |

Silica gel Baker:
[1]60% in $SiO_2$;
[2]90% in $SiO_2$
[3]The product is dried 12 h at 120° C. and then a further 12 h at 550° C.

The composite ZSM-5 zeolite/asbestos precursors were submitted to ion-exchange with a $NH_4Cl$ aqueous solution.

The following example can be considered as typical procedure for the step of ion-exchanging with $NH_4$ ions.

20.0 g of sample A-48 were brought in contact with an aqueous solution of $NH_4Cl$ at 5% by weight, using 10 ml of solution per gram of compound. The suspension was heated at 70°–80° C. under reflux condition and with moderate stirring. After 1 hour of heating, the suspension was allowed to settle and the liquid was then rapidly removed. A fresh volume of $NH_4Cl$ solution was added and the suspension was heated again for another hour. The same procedure was repeated several times so that the entire operation lasted 5 hours.

The suspension was filtered and the solid was washed until $Cl^-$ ions were no longer present in the washings. The compound was dried at 120° C. for 12 hours and activated in the air at 550° C. for 12 hours. The resulting material was the acid form of our composite sample, called HA-48.

Table 5 reports the chemical composition by weight (dried oxide basis), the degree of magnesium leaching (MLD), the Mat/Al ratio, and the degree of crystallinity (DC) of the acid forms of our catalysts: HA stands for composite ZSM-5/asbestos samples under acid forms.

TABLE 5

Physical and Chemical Properties of ZSM-5 and Composite Catalysts

| Catalyst[1] | $SiO_2$ (%) | $Al_2O_3$ (%) | $Na_2O$ (%) | MgO (%) | $Fe_2O_3$ (%) | MLD (%) | Mat/Al | DC (%) |
|---|---|---|---|---|---|---|---|---|
| HP-38 | 98.14 | 3.03 | 0.09 | — | — | — | 28.1 | 100 |
| HP-68 | 97.17 | 2.57 | 0.17 | — | — | — | 32.7 | 100 |
| HA-39 | 95.11 | 2.94 | 0.08 | 1.33 | 0.54 | 97.4 | 28.7 | 86 |
| HA-45 | 90.92 | 2.40 | 0.12 | 3.12 | 3.44 | 93.8 | 34.9 | 91 |
| HA-62 | 91.26 | 3.23 | 0.27 | 3.10 | 2.13 | 93.8 | 26.0 | 100 |
| HA-56 | 90.06 | 3.82 | 0.12 | 3.65 | 2.33 | 92.7 | 22.0 | 86 |
| HA-58 | 86.03 | 2.91 | 0.17 | 5.99 | 4.90 | 88.1 | 28.8 | 88 |
| HA-49 | 84.32 | 3.49 | 0.14 | 6.29 | 5.80 | 87.5 | 23.9 | 90 |
| HA-54 | 83.53 | 3.02 | 0.17 | 6.85 | 6.43 | 86.4 | 27.6 | 86 |
| HA-64 | 85.66 | 2.28 | 0.16 | 7.50 | 4.43 | 85.1 | 36.8 | 96 |
| HA-69 | 81.70 | 3.41 | 0.15 | 7.90 | 6.84 | 84.2 | 24.5 | 99 |
| HA-48 | 82.98 | 3.55 | 0.14 | 7.95 | 5.38 | 84.2 | 23.8 | 84 |
| HA-60 | 81.15 | 2.23 | 0.35 | 9.87 | 6.20 | 80.4 | 38.1 | 83 |

[1]Acid form, dried oxide basis.

The magnesium leaching degree (MLD) is defined as:

$$(MLD) = \frac{(MgO)_i - (MgO)_f}{(MgO)_i} \times 100\%$$

where $(MgO)_i$ and $(MgO)_f$ are the magnesium contents (dried oxide basis) of the asbestos fibres and of the catalyst acid forms, respectively.

The (Mat/Al) ratio is:

$$(Mat/Al) = \frac{SiO_2 + Al_2O_3 + Na_2O + MgO + Fe_2O_3}{(Al)}$$

where $SiO_2$, $Al_2O_3$, $Na_2O$, MgO, $Fe_2O_3$ are the mole fractions, Al the atom fraction in a dehydrated sample.

In the case of composite catalysts of the present invention, this ratio can be seen as proportional to the reciprocal of the aluminum atom concentration, and thus Bronsted acid site concentration:

$$(\text{Mat/Al}) = \frac{\text{constant}}{(H^+)}$$

The (Mat/Al) ratio is equivalent to the (Si/Al) ratio commonly used for pure zeolites.

The degree of crystallinity in the pentasil ZSM-5 zeolite of the present composite samples was determined by measuring the area of the diffraction peaks within the range of the Bragg's angle $2\theta = 22.0 - 25.0°$. To the pure ZSM-5 zeolite sample (HP-38) was assigned the 100% value of ZSM-5 crystallinity. All measurements were done in the presence of an internal standard, $BaCl_2$, which exhibits a strong diffraction peak at $2\theta = 31.0°-32.5°$. The diffraction powder pattern and the DC measurements were obtained by using a Picker X-ray diffractometer, utilizing the Cu-$K_\alpha(\lambda = 1.54$ Å$)$ radiation.

Pure ZSM-5 Zeolite Material

Samples HP-38 and HP-68 were prepared according to a procedure similar to that described in U.S. Pat. No. 3,702,886. Table 4 reports the conditions for synthesizing the ZSM-5 samples. The post-synthesis treatments were identical as in the case of the composite material.

Table 5 reports the chemical composition by weight (dried oxide basis), the Mat/Al ratio and the degree of crystallinity (DC) of the acid forms of our catalysts: HP stands for ZSM-5 zeolite samples under acid form.

Zinc Loading

Zn ions were incorporated to the H-forms of the zeolite or composite material by contacting the solids with an aqueous solution of $ZnCl_2$ under "ion-exchange conditions".

The following examples can be considered as typical of the zinc loading procedure.

(a) HP-68/Zn3 sample:

10 g of HP-68 were brought in contact with an aqueous solution of $ZnCl_2$ (Mallinckrodt) at 2% by weight, using 10 ml of solution per gram of compound. The suspension was heated at 70°–80° C. under reflux and with moderate stirring. After 3 hours of heating, the suspension was allowed to cool down, then filtered and the solid was washed until $Cl^-$ ions were no longer present in the washings. The compound was dried at 120° C. for 12 hours and activated in the air at 550° C. for 12 hours.

(b) HA-69/Zn4 sample:

9 g of HA-69 were brought in contact with an aqueous solution of $ZnCl_2$ (Mallinckrodt) at 0.5% by weight, using 5 ml of solution per gram of compound. The suspension was moderately stirred at ambient temperature for 15 minutes; then it was filtered and the solid was washed until $Cl^-$ ions were no longer present in the washings. The compound was dried at 120° C. for 12 hours and activated in the air at 550° C. for 12 hours.

Table 6 reports the preparation conditions and the chemical composition (MgO, $Fe_2O_3$ and Zn contents) of our Zn loaded samples.

TABLE 6

Preparation of the Zn loaded catalysts

| Catalyst | W in g of acid-catalyst | ZnCl₂ solution concent. (% w/w) | ZnCl₂ solution volume (ml) | Temp. (°C.) | Time | Zn (% w/w) | Fe₂O₃ Present (% w/w) | Fe₂O₃ (Δ) (%) | MgO Present (% w/w) | MgO (Δ) (%) |
|---|---|---|---|---|---|---|---|---|---|---|
| HP-68/Zn2 | 10 | 1 | 50 | 70–80 | 0.5 hr | 0.14 | — | — | — | — |
| HP-68/Zn3 | 13 | 2 | 130 | 70–80 | 3 hr | 0.37 | — | — | — | — |
| HP-68/Zn1 | 10 | 2 | 100 | 70–80 | 7 hr | 0.55 | — | — | — | — |
| HA-62/Zn | 22 | 1 | 110 | 70–80 | 0.5 hr | 0.23 | nr | — | nr | — |
| HA-69/Zn4 | 9 | 0.5 | 45 | ambient | 15 mn | 0.32 | 5.82 | −15 | 8.01 | 0 |
| HA-69/Zn1 | 14 | 1 | 70 | ambient | 0.5 hr | 0.53 | 5.38 | −21 | 7.90 | 0 |
| HA-69/Zn2 | 14 | 1 | 70 | ambient | 1 hr | 0.63 | 4.83 | −29 | 7.83 | 0 |
| HP-69/Zn3 | 9 | 1 | 45 | 70–80 | 0.5 hr | 1.25 | 4.59 | −33 | 7.92 | 0 |
| HA-58/Zn2 | 7.9 | 2 | 39.6 | 70–80 | 0.5 hr | 0.88 | nr | — | nr | — |
| HA-58/Zn1 | 10 | 2 | 100 | 70–80 | 1 hr | 1.36 | nr | — | nr | — |

Δ: percentage loss;
nr = not reported

From these data, the following observations must be made:

with the pure ZSM-5 zeolite sample (HP-68), extremely severe conditions of Zn loading were necessary to obtain a 0.1–0.6% (wt/wt catalyst) metal Zn content. Zn ions were expected to enter into the zeolite structure, mainly to replace part of the $H^+$ acid sites.

With the composite ZSM-5 zeolite sample (HA-69 and others), very mild conditions of Zn loading were necessary to obtain a 0.1–0.6% (wt/wt catalyst) metal Zn content. Zn content increased with the loading operation while Fe oxide content decreased, the MgO content remained nearly constant. This fact suggests a kind of Fe - Zn exchange at the level of the asbestos remnants.

Preparation of the Final Catalysts

The acid or the Zn bearing catalysts were intimately mixed with bentonite (20% by weight) and made into pastes with distilled water (1 ml of water per gram of catalyst). The pastes were pressed into 1 mm O.D. extrudates.

Manganese Loading

In samples where manganese had to be incorporated, the distilled water which was used in the previous procedure for the final catalyst formation, was replaced by an aqueous solution of Mn with an appropriate concentration of $MnCl_2,4H_2O$ from Baker.

Since the amount of the aqueous solution of $MnCl_2$ (in replacement of a corresponding amount of distilled water) was just sufficient to wet the mechanical mixture of "catalyst and bentonite" (technique of dry impregnation), the Mn loading was expected to be effective mostly at the pore openings of the zeolite component.

Table 7 reports the preparation conditions and the Mn content of the final catalysts.

TABLE 7

Preparation of Zn and Mn loaded catalysts
"Dry impregnation conditions"

| Final catalyst | Zn loaded catalyst Zn Content % w/w | W (g) | Bentonite W (g) | MnCl2 solution concentr. % w/w H2O | volume added (ml) | Mn content (metal % w/w) |
|---|---|---|---|---|---|---|
| HP-68/Zn2—Mn2 | 0.14 | 4 | 0.8 | 6 | 3.7 | 1.24 |
| HP-68/Zn3—Mn2 | 0.37 | 4 | 0.8 | 6 | 3.8 | 1.17 |
| HP-68/Zn1—Mn2 | 0.55 | 4 | 0.8 | 6 | 3.7 | 1.72 |
| HA-62/Zn—Mn1 | 0.23 | 4 | 0.8 | 4 | 3.2 | 0.57 |
| HA-62/Zn—Mn2 | 0.23 | 4 | 0.8 | 6 | 3.5 | 1.10 |
| HA-62/Zn—Mn3 | 0.23 | 4 | 0.8 | 10 | 3.6 | 1.79 |
| HA-62/Zn—Mn4 | 0.23 | 4 | 0.8 | 15 | 3.6 | 2.08 |
| HA-69/Zn4—Mn2 | 0.32 | 4 | 0.8 | 6 | 4.0 | 1.60 |
| HA-69/Zn1—Mn2 | 0.53 | 4 | 0.8 | 6 | 4.0 | 1.38 |
| HA-69/Zn1—Mn4 | 0.53 | 4 | 0.8 | 15 | 4.2 | 3.67 |
| HA-58/Zn2—Mn1 | 0.88 | 4.0 | 0.8 | 6 | 3.6 | 1.29 |
| HA-58/Zn1—Mn1 | 1.36 | 4.5 | 0.9 | 6 | 4.4 | 1.15 |

Catalytic Experiments

Catalytic tests were performed by injecting methanol from an injection syringe in an infusion pump into a methanol vaporizer and gas mixer. Nitrogen gas was supplied to the methanol vaporizer and gas mixer from a cylinder connected in-line with a flowmeter. The vaporized methanol was then carried in the nitrogen gas through a catalyst bed set in a catalytic reactor which is itself set inside an oven with automatic thermo-regulation. A chromel-alumel thermocouple was placed in the catalyst bed and was used, in conjunction with a digital thermometer unit, to monitor the temperature of the catalyst bed. The gaseous mixture flowing out of the catalytic reactor was run through a series of condensors maintained at 5°-10° C., to a liquid collector immersed in an ice bath and a cylinder for gas sampling.

The weight hourly space velocity (WHSV) which is defined as:

$$WHSV = \frac{\text{g of injected methanol per hour}}{\text{g of catalyst}}$$

is expressed in $hr^{-1}$.

After a pre-run of 10 minutes, the liquid products were collected and the gaseous ones were analyzed periodically by gas chromatography using a 1.5 m long column packed with the chromosorb P coated with 20% by weight of Squalane. The GC used was a dual FID Hewlett-Packard equipped also with a capillary column (length: 50 m; fused silica coated with a cross-linked polymer) which allowed accurate analyses of the liquid fractions after a run was completed. The composition of the aqueous layer was determined by using a methanol in water external standard.

Table 8 reports the reaction conditions used in the experiments.

TABLE 8

| Reaction conditions | |
|---|---|
| Catalyst weight (dehydrated) | 4 g |
| Temperature (°C.) | 350–500 |
| Total Pressure | 1 atm |
| Methanol Pressure | 0.9 atm |
| Inert gas (stripping gas) | nitrogen |
| W.H.S.V. | 2.4 $hr^{-1}$ |
| Reaction duration | 4 hrs |

Table 9 reports the catalytic data of the nonmodified catalysts at 400° C. with no zinc or manganese. The methanol conversion is the C atom based yield in hydrocarbons. The balance (in C atoms) includes volatile gases ($CO_2$, $H_2$, etc.), dimethyl ether and methanol found in the liquid phase and C deposited onto the catalyst.

It can be expressed as follows:

$$\text{Conversion} = \frac{(NC)_{feed} - (NC)_{Prod}}{(NC)_{feed}} \times 100$$

where $(NC)_{feed}$ is the number of C atoms in the (methanol) feed and $(NC)_{Prod}$ is the number of C atoms in the (hydrocarbon) products.

The product selectivity is expressed as follows:

$$PS(\%) = \frac{\Sigma_i C_i}{\Sigma C} \times 100$$

where $\Sigma C$ and $\Sigma_i C_i$ are the sums of all hydrocarbons produced and of the selected products, respectively.

TABLE 9

Catalytic data of non-modified catalysts at 400° C.

| Catalyst | MLD | Methanol conversion into hydrocarbons (%) | C1-C4 Paraffins | C2-C4 Olefins (OLE) | Aromatics (AR) | Non-Aromatic C5+ | AR/ liquids (%) | durene/ liquids (%) | AR + OLE (%) | OLE + liquids (%) | OLE/ AR |
|---|---|---|---|---|---|---|---|---|---|---|---|
| HP-38 | — | 99 | 35 | 15 | 26 | 24 | 51 | 1.3 | 41 | 65 | 0.58 |
| HP-68 | — | 99 | 31 | 22 | 26 | 21 | 56 | 1.2 | 48 | 69 | 0.85 |
| HA-39 | 97 | 99 | 37 | 13 | 29 | 21 | 57 | 1.3 | 42 | 63 | 0.45 |
| HA-45 | 94 | 99 | 37 | 15 | 27 | 21 | 57 | 1.3 | 42 | 63 | 0.56 |
| HA-62 | 94 | 99 | 28 | 24 | 25 | 23 | 51 | 1.4 | 49 | 72 | 0.96 |
| HA-56 | 93 | 99 | 34 | 17 | 28 | 21 | 57 | 0.7 | 45 | 66 | 0.61 |
| HA-58 | 88 | 99 | 26 | 26 | 24 | 24 | 50 | 1.1 | 50 | 74 | 1.08 |
| HA-49 | 87 | 99 | 20 | 33 | 20 | 27 | 43 | 1.2 | 53 | 80 | 1.65 |
| HA-54 | 86 | 99 | 17 | 37 | 19 | 27 | 41 | 0.9 | 56 | 83 | 1.95 |
| HA-64 | 85 | 99 | 16 | 39 | 18 | 27 | 39 | 1.2 | 57 | 84 | 2.17 |

TABLE 9-continued

| | | Catalytic data of non-modified catalysts at 400° C. | | | | | | | | |
|---|---|---|---|---|---|---|---|---|---|---|
| | | Methanol conversion into hydrocarbons (%) | Product selectivities (%) | | | | | | | |
| Catalyst | MLD | | C$_1$-C$_4$ Paraffins | C$_2$-C$_4$ Olefins (OLE) | Aromatics (AR) | Non-Aromatic C$_5$+ | AR/ liquids (%) | durene/ liquids (%) | AR + OLE (%) | OLE + liquids (%) | OLE/ AR |
| HA-69 | 84 | 99 | 17 | 38 | 18 | 27 | 34 | 1.0 | 56 | 83 | 2.11 |
| HA-48 | 84 | 98 | 16 | 39 | 16 | 29 | 36 | 0.9 | 55 | 84 | 2.44 |
| HA-60 | 80 | 98 | 12 | 44 | 15 | 29 | 34 | 1.2 | 59 | 88 | 2.93 |

Table 10 reports the catalytic data of some of the non-modified catalysts at temperatures higher than 400° C.

Tables 11, 12, 13 and 14 report the catalytic data of all samples in the series HP-68, HA-62, HA-69 and HA-58, respectively.

TABLE 10

| | | | Catalytic data of some non-modified catalysts at 375° C., 450° C. and 500° C. | | | | | | | |
|---|---|---|---|---|---|---|---|---|---|---|
| | | | CH$_3$OH conversion (%) | Product selectivity (%) | | | | Ole + Liq (Liq = Ar + C$_5$+) | | | |
| Catalyst | MLD | T (°C.) | | C$_1$-C$_4$ Paraffins | C$_2$-C$_4$ Olefins (Ole) | Aromatics (Ar) | Non-Aromatics C$_5$+ | | Ole + Ar | Ole/Ar | Durene/Liq |
| HP-38 | — | 375 | 98 | 31 | 17 | 26 | 26 | 69 | 43 | 0.7 | 1.3 |
| HA-39 | 97 | 375 | 99 | 37 | 11 | 28 | 24 | 63 | 39 | 0.4 | 1.4 |
| HA-45 | 94 | 375 | 99 | 37 | 11 | 29 | 23 | 63 | 40 | 0.4 | 1.6 |
| HA-58 | 88 | 375 | 99 | 30 | 18 | 27 | 25 | 70 | 45 | 0.7 | 1.8 |
| HA-48 | 84 | 375 | 97 | 16 | 34 | 16 | 34 | 84 | 50 | 2.1 | 1.4 |
| HA-60 | 80 | 375 | 80 | 9 | 41 | 14 | 36 | 91 | 55 | 2.9 | 2.0 |
| HP-38 | — | 450 | 96 | 24 | 38 | 19 | 19 | 76 | 57 | 2.0 | 1.2 |
| HA-45 | 94 | 450 | 99 | 24 | 36 | 22 | 18 | 76 | 58 | 1.6 | 0.9 |
| HA-58 | 88 | 450 | 99 | 17 | 47 | 17 | 19 | 83 | 64 | 2.8 | 0.6 |
| HA-60 | 80 | 450 | 98 | 5 | 63 | 13 | 19 | 95 | 76 | 4.9 | 1.1 |
| HA-60 | 80 | 500 | 99 | 4 | 73 | 11 | 12 | 96 | 84 | 6.6 | 0.6 |

TABLE 11

| | | | | Catalytic data of the pure ZSM-5 based catalysts (series HP-68) | | | | | | | |
|---|---|---|---|---|---|---|---|---|---|---|---|
| | | | | CH$_3$OH conversion | | Product Selectivity (%) | | | Ole + Liq. (Liq = Ar + C$_5$+) | | | |
| Catalyst | Zn (%) | Mn (%) | T (°C.) | (%) | (Δ) (%) | C$_1$-C$_4$ Paraf. | C$_2$-C$_4$ Olefins (Ole) | Aromatics (Ar) | Non-Arom. C$_5$ + | | Ole + Ar | Ole/ Ar | Durene/ Liq |
| HP-68 | — | — | 400 | 99 | 0 | 31 | 22 | 26 | 21 | 69 | 48 | 0.9 | 1.2 |
| HP-68/Zn2 | 0.14 | — | 400 | 99 | 0 | 28 | 23 | 27 | 22 | 72 | 50 | 0.9 | 1.6 |
| HP-68/Zn2—Mn2 | 0.14 | 1.24 | 400 | 99 | 0 | 19 | 36 | 22 | 23 | 81 | 58 | 1.6 | 1.5 |
| HP-68/Zn3 | 0.37 | — | 400 | 99 | 0 | 22 | 22 | 36 | 20 | 78 | 58 | 0.6 | 1.7 |
| HP-68/Zn3—Mn2 | 0.37 | 1.17 | 400 | 99 | 0 | 11 | 37 | 31 | 21 | 89 | 68 | 1.2 | 2.4 |
| HP-68/Zn1 | 0.55 | — | 400 | 99 | 0 | 18 | 27 | 35 | 20 | 82 | 62 | 0.8 | 2.4 |
| HP-68/Zn1—Mn2 | 0.55 | 1.72 | 400 | 94 | −5 | 8 | 41 | 25 | 26 | 92 | 66 | 1.6 | 3.5 |
| HP-68 | — | — | 450 | 99 | 0 | 25 | 32 | 23 | 20 | 75 | 55 | 1.4 | 1.2 |
| HP-68/Zn2 | 0.14 | — | 450 | 99 | 0 | 20 | 36 | 26 | 18 | 80 | 62 | 1.4 | 1.1 |
| HP-68/Zn2—Mn2 | 0.14 | 1.24 | 450 | 97 | −2 | 11 | 48 | 25 | 16 | 89 | 73 | 1.9 | 1.3 |
| HP-68/Zn3 | 0.37 | — | 450 | 97 | −2 | 12 | 36 | 37 | 15 | 88 | 80 | 1.0 | 1.6 |
| HP-68/Zn3—Mn2 | 0.37 | 1.17 | 450 | 93 | −6 | 6 | 46 | 33 | 15 | 94 | 79 | 1.4 | 2.4 |
| HP-68/Zn1 | 0.55 | — | 450 | 91 | −8 | 9 | 38 | 38 | 15 | 91 | 76 | 1.0 | 3.6 |
| HP-68/Zn1—Mn2 | 0.55 | 1.72 | 450 | 36 | −13 | 6 | 43 | 35 | 16 | 94 | 78 | 1.2 | 3.8 |

TABLE 12

| | | | | Catalytic data of the composite ZSM-5/asbestos catalysts (series HA-62) | | | | | | | | |
|---|---|---|---|---|---|---|---|---|---|---|---|---|
| | | | | CH$_3$OH conversion | | Product Selectivity (%) | | | | Ole + Liq. (Liq = Ar + C$_5$+) | | | |
| Catalyst | Zn (%) | Mn (%) | T (°C.) | (%) | (Δ) (%) | C$_1$-C$_4$ Paraf. | C$_2$-C$_4$ Olefins (Ole) | Aromatics (Ar) | Non-Arom. C$_5$ + | | Ole + Ar | Ole/ Ar | Durene/ Liq |
| HA-62 | — | — | 400 | 99 | 0 | 28 | 24 | 24 | 24 | 72 | 48 | 1.0 | 1.4 |
| HA-62/Zn | 0.23 | — | 400 | 99 | 0 | 20 | 27 | 32 | 21 | 80 | 59 | 0.8 | 2.1 |
| HA-62/Zn—Mn1 | 0.23 | 0.57 | 400 | 99 | 0 | 10 | 37 | 34 | 19 | 90 | 71 | 1.1 | 2.0 |
| HA-62/Zn—Mn2 | 0.23 | 1.10 | 400 | 97 | −2 | 10 | 38 | 28 | 24 | 90 | 66 | 1.4 | 2.0 |
| HA-62/Zn—Mn3 | 0.23 | 1.79 | 400 | 97 | −2 | 7 | 42 | 24 | 27 | 93 | 66 | 1.8 | 2.1 |
| HA-62/Zn—Mn4 | 0.23 | 2.08 | 400 | 98 | −1 | 7 | 47 | 21 | 25 | 93 | 68 | 2.2 | 1.7 |
| HA-62 | — | — | 450 | 99 | 0 | 22 | 41 | 20 | 17 | 78 | 61 | 2.1 | 0.8 |
| HA-62/Zn | 0.23 | — | 450 | 99 | 0 | 11 | 40 | 37 | 12 | 89 | 77 | 1.1 | 1.6 |
| HA-62/Zn—Mn1 | 0.23 | 0.57 | 450 | 98 | −1 | 7 | 43 | 39 | 11 | 93 | 82 | 1.1 | 2.7 |
| HA-62/Zn—Mn2 | 0.23 | 1.10 | 450 | 96 | −3 | 6 | 45 | 35 | 14 | 94 | 80 | 1.3 | 2.4 |
| HA-62/Zn—Mn3 | 0.23 | 1.79 | 450 | 98 | −1 | 5 | 52 | 28 | 15 | 95 | 80 | 1.8 | 2.3 |
| HA-62/Zn—Mn4 | 0.23 | 2.08 | 450 | 97 | −2 | 5 | 50 | 32 | 13 | 95 | 82 | 1.6 | 3.1 |

TABLE 13

Catalytic data of the composite ZSM-5/asbestos catalysts (series HA-69)

| Catalyst | Zn (%) | Mn (%) | T (°C.) | CH3OH conversion (%) | (Δ) (%) | C1–C4 Paraf. | C2–C4 Olefins (Ole) | Aromatics (Ar) | Non-Arom. C5+ | Ole + Liq. (Liq = Ar + C5+) | Ole + Ar | Ole/ Ar | Durene/ Liq |
|---|---|---|---|---|---|---|---|---|---|---|---|---|---|
| HA-69 | — | — | 400 | 99 | 0 | 17 | 38 | 18 | 27 | 83 | 56 | 2.1 | 1.0 |
| HA-69/Zn4 | 0.32 | — | 400 | 98 | −1 | 7 | 44 | 27 | 22 | 93 | 71 | 1.6 | 2.4 |
| HA-69/Zn4—Mn2 | 0.32 | 1.60 | 400 | 91 | −8 | 5 | 50 | 18 | 27 | 95 | 68 | 2.8 | 2.2 |
| HA-69/Zn1 | 0.53 | — | 400 | 90 | −9 | 6 | 46 | 25 | 23 | 94 | 71 | 1.8 | 2.7 |
| HA-69/Zn1—Mn2 | 0.53 | 1.38 | 400 | 79 | −20 | 6 | 52 | 16 | 26 | 94 | 68 | 3.3 | 2.8 |
| HA-69/Zn1—Mn4 | 0.53 | 3.67 | 400 | 75 | −24 | 6 | 56 | 11 | 27 | 94 | 67 | 5.1 | 1.9 |
| HA-69 | — | — | 450 | 99 | 0 | 13 | 55 | 15 | 17 | 87 | 70 | 3.7 | 0.8 |
| HA-69/Zn4 | 0.32 | — | 450 | 82 | −17 | 9 | 46 | 31 | 14 | 91 | 77 | 1.5 | 0.4 |
| HA-69/Zn4—Mn2 | 0.32 | 1.60 | 450 | 86 | −13 | 6 | 51 | 25 | 18 | 94 | 76 | 2.0 | 2.7 |
| HA-69/Zn1 | 0.53 | — | 450 | 70 | −29 | 9 | 49 | 31 | 11 | 91 | 80 | 1.6 | 3.7 |
| HA-69/Zn1—Mn2 | 0.53 | 1.38 | 450 | 75 | −24 | 9 | 54 | 23 | 14 | 91 | 77 | 2.3 | 3.5 |
| HA-69/Zn1—Mn4 | 0.53 | 3.63 | 450 | 80 | −19 | 6 | 53 | 24 | 17 | 94 | 77 | 2.2 | 2.7 |

Discussions on the Catalytic Performances

By leaching out part of the magnesium (and iron) from the asbestos fibers and then by crystallizing in situ the ZSM-5 zeolite within the more or less degraded fibers, we have prepared precursor material for very selective catalysts. In fact, while a high leaching degree (MLD≧90%) led to a similar product distribution as in pure ZSM-5 zeolite samples, more light olefins were produced mainly at the expenses of light paraffins, with lower MLD (from 75% to 90%) (see Table 9). In particular the medium-leached HA-60 sample (MLD=80%) exhibits very high selectivity in light olefins at 500° C. with no loss in the methanol conversion into hydrocarbons (close to 100%) (see Table 10).

On both ZSM-5 zeolite and composite zeolite-asbestos catalysts, the Zn loading under "ion-exchange" conditions and not exceeding 0.5% (wt/wt) provided a significant increase in liquid (and aromatic) hydrocarbon yield without depleting the methanol conversion (see Tables 11, 12 and 13). When the Zn loading exceeded 0.5 there was a significant loss in the methanol conversion at 400° C. (loss of less 20% if the Zn loading ranged between 0.5 and 1.0%). This is shown in Table 14.

The Mn incorporation by "dry impregnation" compressed furtherly the light paraffin formation and varied smoothly the Ole/Ar ratio (depending upon the Mn content of the final catalysts) without practically changing the cumulative production of "Ole+Ar" and "Ole+Liq" (see Tables 11, 12, 13 and 14). This flexibility in the interconversion of light olefins-aromatics is extremely important in terms of industrial application.

I claim:

1. A pentasil zeolite-asbestos composite catalyst comprising a magnesium, and iron leached asbestos micromatrix having a crystallized pentasil zeolite within its micro-matrix, said pentasil zeolite having a portion of its internal acid reaction sites replaced with zinc ions and having manganese ions adsorbed on the external surface thereof, said magnesium and iron leached asbestos micro-matrix is doped internally with zinc ions and externally with manganese ions, the amount of zinc ions being from 0.1 to 0.5% w/w of the metal content and the amount of manganese being from 0.2 to 5.0% w/w of the metal content.

2. The catalyst of claim 1, wherein the amount of zinc is from 0.1 to 0.6% w/w and the amount of manganese is from 0.2 to 2.5% w/w.

3. The catalyst of claim 2, wherein the amount of zinc is 0.37% w/w and the amount of manganese is 1.17% w/w.

4. The catalyst of claim 2, wherein the amount of zinc is 0.23% w/w and the amount of manganese is 1.10% w/w.

5. The catalyst of claim 2, wherein the amount of zinc is 0.23% w/w and the amount of manganese is 2.08% w/w.

6. The catalyst of claim 2, wherein the amount of zinc is 0.32% w/w and the amount of manganese is 1.60% w/w.

TABLE 14

Catalytic data of the composite ZSM-5/asbestos catalysts (series HA-58)

| Catalyst | Zn (%) | Mn (%) | T (°C.) | CH3OH conversion (%) | (Δ) (%) | C1–C4 Paraf. | C2–C4 Olefins (Ole) | Aromatics (Ar) | Non-Arom. C5+ | Ole + Liq. (Liq = Ar + C5+) | Ole + Ar | Ole/ Ar | Durene/ Liq |
|---|---|---|---|---|---|---|---|---|---|---|---|---|---|
| HA-58 | — | — | 400 | 99 | 0 | 27 | 26 | 23 | 24 | 73 | 49 | 1.1 | 1.0 |
| HA-58/Zn2 | 0.88 | — | 400 | 86 | −13 | 10 | 32 | 45 | 13 | 90 | 77 | 0.7 | 3.8 |
| HA-58/Zn2—Mn1 | 0.88 | 1.29 | 400 | 88 | −11 | 5 | 38 | 41 | 16 | 95 | 79 | 0.9 | 4.6 |
| HA-58/Zn1 | 1.36 | — | 400 | 94 | −5 | 8 | 35 | 41 | 16 | 92 | 76 | 0.9 | 5.0 |
| HA-58/Zn1—Mn1 | 1.36 | 1.15 | 400 | 79 | −20 | 4 | 46 | 31 | 19 | 96 | 77 | 1.5 | 5.7 |
| HA-58 | — | — | 450 | 99 | 0 | 17 | 47 | 17 | 19 | 83 | 64 | 2.8 | 5.8 |
| HA-58/Zn2 | 0.88 | — | 450 | 38 | −62 | 15 | 43 | 37 | 5 | 85 | 80 | 1.2 | 6.2 |
| HA-58/Zn2—Mn1 | 0.88 | 1.29 | 450 | 53 | −47 | 7 | 37 | 48 | 8 | 93 | 85 | 0.8 | 4.5 |
| HA-58/Zn1 | 1.36 | — | 450 | 31 | −69 | 10 | 30 | 54 | 6 | 90 | 84 | 0.6 | 5.4 |
| HA-58/Zn1—Mn1 | 1.36 | 1.15 | 450 | 50 | −50 | 10 | 55 | 30 | 5 | 90 | 85 | 1.8 | 5.7 |

* * * * *

UNITED STATES PATENT AND TRADEMARK OFFICE
CERTIFICATE OF CORRECTION

PATENT NO. : 4,615,995
DATED      : Oct. 7, 1986
INVENTOR(S) : LE VAN MAO

It is certified that error appears in the above-identified patent and that said Letters Patent is hereby corrected as shown below:

On the front page, at the line [22] Filed:, change the filing date from "Jan. 3, 1984" to --Jan. 3, 1985--.

Signed and Sealed this

Twentieth Day of October, 1987

*Attest:*

DONALD J. QUIGG

*Attesting Officer*

*Commissioner of Patents and Trademarks*